United States Patent
Hata et al.

(10) Patent No.: US 6,756,472 B1
(45) Date of Patent: Jun. 29, 2004

(54) PROCESS FOR PRODUCING POLYMER

(75) Inventors: Yoshio Hata, Ibaraki (JP); Yasutaka Igari, Kobe (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/857,943

(22) PCT Filed: Dec. 14, 1999

(86) PCT No.: PCT/JP99/07013

§ 371 (c)(1),
(2), (4) Date: Jun. 12, 2001

(87) PCT Pub. No.: WO00/35990

PCT Pub. Date: Jun. 22, 2000

(30) Foreign Application Priority Data

Dec. 15, 1998 (JP) ............................................ 10-356497

(51) Int. Cl.$^7$ ................................................ C08G 63/08
(52) U.S. Cl. ........................ 528/354; 528/359; 525/411; 525/413; 525/415
(58) Field of Search ................................ 528/354, 359, 528/271, 272, 365; 525/411, 413, 415

(56) References Cited

FOREIGN PATENT DOCUMENTS

| EP | 0 601 799 | 6/1994 |
|---|---|---|
| EP | 668073 A2 | 8/1995 |
| EP | 0 668 073 | 8/1995 |
| EP | 0 839 525 | 5/1998 |
| EP | 1 048 301 A1 | 11/2000 |
| EP | 1 197 208 | 4/2002 |
| WO | 95/03356 | 2/1995 |
| WO | 99/36099 | 7/1999 |

OTHER PUBLICATIONS

Database—Chemical Abstracts, Akira Saikawa et al., Sustained Release Compositions, "Process for Producing the Same and Utilization Thereof", Database Accession No. 131:106841, XP00222246 *abstract*.
Verified English Translation of Japanese Application No. 6412/98 filed on Jan. 16, 1998.
Verified English Translation of priority document No. 356497/1998 filed Dec. 15, 1998.

*Primary Examiner*—P. Hampton Hightower
(74) *Attorney, Agent, or Firm*—Wenderoth, Lind & Ponack, L.L.P.

(57) ABSTRACT

A process for producing a biodegradable polymer having free carboxyl at the ω-end charcterized by polymerizing a cyclic ester compound in the presence of a hydroxymonocarboxylic acid derivative having protected carboxyl or a hydroxydicarboxylic acid derivative having protected carboxyl, and then deprotecting the thus obtained polymer having protected carboxyl at the ω-end. Use of the above process makes it easy to control the molecular weight of the target biodegradable polymer and the content of free carboxyl therein, thereby enabling the efficient production of a polymer having a high purity and being contaminated with littel catalyst remaining therein.

10 Claims, No Drawings

PROCESS FOR PRODUCING POLYMER

This application is a 371 of PCT/JP99/07013 filed Dec. 14, 1999.

TECHNICAL FIELD

The present invention relates to a process for producing a novel biodegradable polymer.

BACKGROUND ART

EP-A-0839525 discloses a sustained-release preparation composed of a physiologically active peptide or its salt and a biodegradable polymer, and its production process, and the biodegradable polymer described in the publication is produced by subjecting a biodegradable polymer produced by a known ring-opening polymerization process to a hydrolysis process which itself is known.

The ring-opening polymerization process uses a cyclic dimer of lactic acid by adding a catalyst while heating, and this process is described by J. H. R. Woodland et al. in the Journal of Medicinal Chemistry (J. Med. Chem.), Vol. 16, page 897 (1973). In addition, a process in which this is performed using a catalyst from a cyclic diester compound such as a lactide or glycolide is described in the Encyclopedic Handbook of Biomaterials and Bioengineering Part A: Materials, Vol. 2, Marcel Dekker, Inc. (1995).

Further, a process of producing a block copolymer in which one polylactide and three dextrans are bonded through citric acid by polymerization of tribenzyl citrate and lactide is described in WO 95/03356.

Since polymers obtained by the above known ring-opening polymerization process do not always have a free carboxyl group at the ω-end of the resulting polymer, it is difficult to efficiently incorporate a physiologically active substance into a sustained-release preparation. In addition, it is difficult to adjust the molecular weight of the target biodegradable polymer at the raw material loading stage.

Thus, there has been a need to establish a process of producing a biodegradable polymer that allows a physiologically active substance to be efficiently incorporated into a sustained-release preparation and facilitates easy adjustment of the molecular weight of the target biodegradable polymer.

In addition, there has also been a need to establish a production process suited for a biodegradable polymer used in a sustained-release preparation that releases a physiologically active substance over a long time of at least about six months or more.

DISCLOSURE OF THE INVENTION

As a result of intensive study to solve the above problems, the present inventors found a production process of a biodegradable polymer having a free carboxyl group at the ω-end comprising subjecting a cyclic ester compound to a polymerization reaction in the presence of a hydroxymonocarboxylic acid derivative in which the carboxyl group is protected or a hydroxydicarboxylic acid derivative in which the carboxylic acid groups are protected, and subjecting the resulting polymer having a protected carboxyl group at the ω-end to a deprotecting reaction. The present inventors further studied and, thus, the present invention was accomplished.

Namely, the present invention relates to the following:
(1) A process for producing a biodegradable polymer having a free carboxyl group at the ω-end comprising:
  subjecting a cyclic ester compound to a polymerization reaction in the presence of a hydroxymonocarboxylic acid derivative in which the carboxyl group is protected, or a hydroxydicarboxylic acid derivative in which the carboxyl groups are protected, and
  subjecting the resulting polymer having a protected carboxyl group at the ω-end to a deprotecting reaction;
(2) The process described in (1), wherein the hydroxymonocarboxylic acid derivative in which the carboxyl group is protected is glycolic acid in which the carboxyl group is protected, L-lactic acid in which the carboxyl group is protected, D-lactic acid in which the carboxyl group is protected, or DL-lactic acid in which the carboxyl group is protected;
(3) The process described in (1), wherein the protecting group of the hydroxymonocarboxylic acid in which the carboxyl group is protected is a tert-butyl group or benzyl group;
(4) The process described in (1), wherein the hydroxydicarboxylic acid derivative in which the carboxyl groups are protected is dibenzyl tartronate or di-tert-butyl 2-hydroxyethylmalonate;
(5) The production process described in (1), wherein the cyclic ester compound is a cyclic monoester compound or a cyclic diester compound;
(6) The production process described in (1), wherein the deprotecting reaction is an acidolysis reaction;
(7) A process for producing a biodegradable polymer having a free carboxyl group at the ω-end comprising: subjecting a cyclic ester compound to a polymerization reaction in the presence of a hydroxymonocarboxylic acid derivative in which the carboxyl group is protected, and subjecting the resulting polymer having a protected carboxyl group at the ω-end to a deprotecting reaction;
(8) The process described in (7), wherein an acid hydrolysis reaction is carried out following the deprotecting reaction;
(9) The process described in (1) or (7), wherein the biodegradable polymer is a biodegradable polymer that is used in a sustained-release preparation that releases a physiologically active substance over the course of at least about six months;
(10) A biodegradable polymer obtained by the production process described in (1) or (7);
(11) A sustained-release preparation containing the biodegradable polymer described in (10);
(12) The sustained-release preparation described in (11) further containing a physiologically active substance; and
(13) The sustained-release preparation described in (12), wherein the physiologically active substance is an LH-RH derivative or its salt.

BEST EMBODIMENT FOR CARRYING OUT THE INVENTION

There are no particular restrictions on the physiologically active substance used in the present invention provided it is useful pharmacologically; it may be a non-peptide compound or peptide compound. Examples of non-peptide compounds include agonists, antagonists and compounds having enzyme inhibitory action. In addition, examples of peptide compounds preferably include physiologically active peptides having a molecular weight from about 300 to about 400,000, preferably from about 400 to about 30,000, more preferably from about 500 to about 25,000, and particularly preferably from about 500 to about 20,000.

Examples of the physiologically active peptides include leuteinizing hormone releasing hormone (LH-RH) insulin, somatostatin, growth hormone, growth hormone releasing hormone (GH-RH), prolactin, erythropoietin, adrenocortical hormone, melanocyte stimulating hormone, thyroid hormone releasing hormone, thyroid stimulating hormone, leuteinizing hormone, follicle-stimulating hormone, vasopressin, oxytocin, calcitonin, gastrin, secretin, pancreozymin, cholestokinin, angiotensin, human placental lactogen, human chorionic gonadotropin, enkephalin, endorphin, kyotorphin, tuftsin, thymopoietin, thymosin, thymosthymlin, thymic humoral factor, serum thymic factor, tumor necrosis factor, colony stimulating factor, motilin, dynorphin, bombesin, neurotensin, caerulein, bradykinin, atrial natriuretic factor, neural growth factor, cell growth factor, neurotrophic factor and peptides having endoserine antagonistic action, their derivatives as well as their fragments or derivatives of their fragments.

The physiologically active peptide used in the present invention may itself be a pharmacologically acceptable salt. In the case the physiologically active peptide has a basic group such as an amino group, examples of such salts include the salts of inorganic acids (e.g., carbonic acid, bicarbonic acid, hydrochloric acid, sulfuric acid, nitric acid and boric acid) and organic acids (e.g., succinic acid, acetic acid, propionic acid and trifluoroacetic acid).

In the case the physiologically active peptide has an acidic group such as a carboxyl group, examples of such salts include the salts of inorganic bases (e.g., alkali metals such as sodium and potassium, and alkaline earth metals such as calcium and magnesium), and organic bases (e.g., organic amines such as triethylamine and basic amino acids such as arginine). In addition, the physiologically active peptide may form a metal complex compound (e.g, copper complex or zinc complex).

A preferable example of the above physiologically active peptides is an LH-RH derivative, examples of which include LH-RH derivatives and their salts effective for contraception and against sex hormone-dependent diseases such as prostatic cancer, prostatic hypertrophy, endometriosis, hysteromyoma, precocious puberty and breast cancer.

Specific examples of LH-RH derivatives or their salts include the peptides described in, for example, Treatment with GnRH Analogs: Controversies and Perspectives (The Parthenon Publishing Group Ltd., 1996), JP 3-503165 A, JP 3-101695 A, JP 7-97334 A and JP 8-259460 A.

Examples of LH-RH derivatives also include LH-RH agonists and LH-RH antagonists. A preferable example of an LH-RH antagonist is the physiologically active peptide or its salt represented by the general formula (I):

X-D2Nal-D4ClPhe-D3Pal-Ser-A-B-Leu-C-Pro-DA1aNH$_2$ (wherein, X represents N(4H$_2$-furoyl)Gly or NAc, A represents a residue selected from NMeTyr, Tyr, Aph(Atz) and NMeAph (Atz), B represents a residue selected from DLys (Nic), DCit, DLys(AzaglyNic), DLys(AzaglyFur), DhArg (Et$_2$), DAph(Atz) and DhCi, and C represents Lys(Nisp), Arg or Arg(Et$_2$)).

A preferable example of an LH-RH agonist that is used is the physiologically active peptide or its salt represented by the general formula (II):

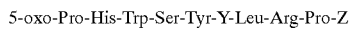

5-oxo-Pro-His-Trp-Ser-Tyr-Y-Leu-Arg-Pro-Z (wherein, Y represents a residue selected from DLeu, DAla, DTrp, DSer(tBu), D2Nal and DHis(ImBzl), and Z represents NH—C$_2$H$_5$ or Gly-NH$_2$). In particular, a peptide wherein Y is DLeu and Z is NH—C$_2$H$_5$ (namely, the peptide represented by 5-oxo-Pro-His-Trp-Ser-Tyr-DLeu-Leu-Arg-Pro-NH—C$_2$H$_5$, and its acetate in particular) is preferable.

These peptides can be produced using the processs described in the previously mentioned references or patent publications, or processs complying with those processs.

The meanings of abbreviations used in the present specification are as indicated below.

Abbreviation Name
N(4H$_2$-furoyl)Gly: N-tetrahydrofuroylglycine residue
NAc: N-acetyl group
D2Nal: D-3-(2-naphthyl)alanine residue
D4ClPhe: D-3-(4-chloro)phenylalanine residue
D3Pal: D-3-(3-pyridyl)alanine residue
NMeTyr: N-methyltyrosine residue
Aph(Atz): N-[5'-(3'-amino-1'H-1',2',4'-triazolyl)]-phenylalanine residue
NMeAph(Atz): N-methyl-[5'-(3'-amino-1'H-1',2',4'-triazolyl)]phenylalanine residue
DLys(Nic): D-(e-N-nicotinoyl)lysine residue
Dcit: D-citrulline residue
DLys(AzaglyNic): D-(azaglycylnicotinoyl)lysine residue
DLys(AzaglyFur): D-(azaglycylfuranyl)lysine residue
DhArg(Et$_2$): D-(N,N'-diethyl)homoarginine residue
DAph(Atz): D-N-[5'-(3'-amino-1'H-1',2',4'-triazolyl)]-phenylalanine residue
DhCi: D-homocitrulline residue
Lys(Nisp): (e-N-isopropyl)lysine residue
hArg(Et$_2$) (N,N'-diethyl)homoarginine residue
Dser(tBu): D-O-(t-butyl)serine residue
DHis(ImBzl): N$^1$-benzylhistidine residue In the case of indicating other amino acids with abbreviations, the abbreviations are based on abbreviations according to the IUPAC-IUB Commission on Biochemical Nomenclature (European Journal of Biochemistry, Vol. 138, pp. 9–37 (1984)), or on commonly used abbreviations in the relevant field. In addition, in the case there is the possibility of existence of optical isomers of amino acids, the L-form is indicated unless otherwise indicated.

In addition to a physiologically active substance, the sustained-release preparation of the present invention may also contain, for example, dispersants (including surfactants such as Tween 80 and HCO-60; polysaccharides such as carboxymethyl cellulose, sodium alginate and sodium hyaluronate; protamine sulfate and polyethylene glycol 400), preservatives (such as methyl paraben and propyl paraben), isotonic agents (such as sodium sulfate, mannitol, sorbitol and glucose), fats and oils (such as sesame oil and corn oil), phospholipids (such as lecithin), excipients (such as lactose, cornstarch, mannitol and cellulose), binders (such as sucrose, gum arabic, methyl cellulose, carboxymethyl cellulose and dextrin), disintegrating agents (such as calcium carboxymethyl cellulose), and drug retention agents (such as gelatin, hydroxynaphthoic acid and salicylic acid).

Examples of biodegradable polymers used in the present invention include polymers, copolymers or their mixtures having a free carboxyl group at the ω-end (such as polyhydroxycarboxylic acid in which the ω residue is glycolic acid, polyhydroxycarboxylic acid in which the ω residue is DL-lactic acid, polyhydroxycarboxylic acid in which the ω residue is D-lactic acid, polyhydroxycarboxylic acid in which the ω residue is L-lactic acid, polyhydroxycarboxylic acid in which the ω residue is tartronic acid, and polyhydroxycarboxylic acid in which the ω residue is 2-hydroxyethylmalonic acid) which are synthesized from one or more kinds of derivatives in which the carboxyl group of a hydroxymonocarboxylic acid (such as glycolic acid or lactic acid) is protected (such as glycolic acid in which the carboxyl group is protected, L-lactic acid in which the carboxyl group is protected, D-lactic acid in which the carboxyl group is protected, and DL-lactic acid in which the carboxyl group is protected (examples of protecting groups include a tert-butyl group and a benzyl group), and more specifically, tert-butyl D-lactate and benzyl L-lactate), derivatives in which the carboxyl group of a hydroxydicarboxylic acid (such as tartronic acid or 2-hydoxyethylmalonic acid) is protected (such as dibenzyl tartronate and di-tert-butyl 2-hydroxyethylmalonate) and so forth, and one or more kinds of cyclic ester compounds (such as cyclic diester compounds (lactides) and cyclic monoester compounds (lactones)).

The portion of the "polyhydroxycarboxylic acid" other than the ω residue is preferably poly-α-hydroxycarboxylic acid.

Preferable examples of the α-hydroxycarboxylic acid that serves as the minimum repeating unit of the "poly-α-hydroxycarboxylic acid" include lactic acid and glycolic acid, as well as their copolymers (which may be referred to as poly(lactide-co-glycolide), poly(lactic acid-co-glycolic acid) or lactic acid-glycolic acid polymer, and unless otherwise indicated, generically referred to as homopolymers of lactic acid and glycolic acid (also referred to as polymers, polylactides or polyglycolides) and copolymers).

Although there are no particular restrictions on the composite ratio (lactic acid/glycolic acid) (mol/mol %) of the "lactic acid-glycolic acid polymer" provided the object of the present invention is achieved, a composite ratio of about 100/0 to about 30/70 is used. A preferable example of the composite ratio is about 100/0 to about 40/60, and a composite ratio of about 100/0 to about 45/55 is used particularly commonly.

In the case the α-hydroxycarboxylic acid that serves as the minimum repeating unit of the "poly-α-hydroxycarboxylic acid" has an optically active center within the molecule, although it may be any of the D-form, L-form or D,L-form, the ratio of the D-form to the L-form (D-form/L-form) (mol/mol %) is preferably within the range of about 75/25 to about 25/75. This D-form/L-form ratio (mol/mol %) is used particularly commonly within a range of about 60/40 to about 30/70.

Normally, the weight average molecular weight of the above biodegradable polymer is preferably about 3,000 to about 500,000, more preferably about 3,000 to about 200,000, and particularly preferably about 3,000 to about 100,000.

In addition, normally the degree of dispersion (weight average molecular weight/number average molecular weight) is preferably about 1.2 to about 4.0, and particularly preferably about 1.5 to 3.5.

In the case the ω residue of the above biodegradable polymer is a monocarboxyl group, normally the amount of the terminal carboxyl group per unit mass of polymer is preferably about 40 to about 90 μmol/g and particularly preferably about 50 to about 90 μmol/g.

In the case the ω-residue of the above biodegradable polymer is a dicarboxyl group, normally the amount of the terminal carboxyl group per unit mass of polymer is preferably about 30 to about 800 μmol/g, and particularly preferably about 60 to about 400 μmol/g.

The above weight average molecular weight, number average molecular weight and degree of dispersion are referred to as the molecular weights in terms of polystyrene as measured by gel permeation chromatography (GPC) using for the reference substance 11 types of monodispersed polystyrene having weight average molecular weights of 455645, 354000, 98900, 66437, 37200, 17100, 9830, 5870, 2500, 1303 and 504, and the calculated degree of dispersion. Measurement is performed using a high-speed GPC system (Tosoh: HLC-812OGPC), GPC column KF804L×2 (Showa Denko) and using chloroform for the mobile phase.

The above-described amount of terminal carboxyl group refers to that which is determined by terminal group assay according to the labeling process. More specifically, in the case of a polymer in which the ω residue is lactic acid, biodegradable polymer Wmg is dissolved in 2 ml of a mixed liquid of 5 N HCl/acetonitrile (v/v=4/96) followed by the addition of 2 ml of 0.01 M o-nitrophenylhydrazine (ONPH) solution (5 N HCl/acetonitrile/ethanol=1.02/35/15) and 2 ml of 0.15 M EDC solution (pyridine/ethanol=4v/96v) and distilling off the solvent after reacting at 40° C. for 30 minutes. After the residue is washed with water (4 times), the thus treated residue is dissolved in 2 ml of acetonitrile, followed by addition of 0.5 mol/l of an aqueous ethanolic potassium hydroxide, to effect reaction at 60° C. for 30 minutes. The reaction liquid is diluted with 1.5 N NaOH to obtain Y ml and absorbance A (/cm) at 544 nm is measured using 1.5 N NaOH as the reference. On the other hand, the amount of free carboxyl group [COOH] of a polymer in which the ω residue is lactic acid is determined using the equation below when the amount of free carboxyl group C mol/L is determined using aqueous DL-lactic acid solution as the standard substance by NaOH titration, and the absorbance at 544 nm when using DL-lactic acid hydazide with the. ONPH labeling process is taken to be B (/cm).

$$[COOH](mol/g) = (AYC)/(WB)$$

In addition, the amount of terminal carboxyl group can be calculated by dissolving a biodegradable polymer in a mixed solvent of toluene, acetone and methanol, and titrating this solution with an aqueous alcoholic potassium hydroxide solution using phenolphthalein as the indicator.

Although the degradation and disappearance rate of biodegradable polymer varies considerably according to the copolymerization composition, molecular weight or amount of free carboxyl group, in general, the release time can be lengthened by increasing molecular weight and reducing the amount of free carboxyl group. However, a minimum predetermined amount of free carboxyl group is required since it has an effect on the efficiency by which a physiologically active substance is incorporated into the preparation. For this reason, in order to provide a biodegradable polymer for a long-term sustained-release preparation (for example, at least about 6 months or more, preferably about 6 months (26 weeks) to about 8 months (35 weeks), more preferably about 6 months (26 weeks) to about 7 months (30 weeks), and particularly preferably about 6 months (26 weeks) to about 6.5 months (28 weeks)), it is preferable that the ω-end be poly-DL-lactic acid, a monocarboxyl group, that the above weight average molecular weight be about 20,000 to about 50,000, and that the amount of free carboxyl group be about 50 to about 90 μmol/g.

The following provides a detailed description of the production process of the biodegradable polymer of the present invention.

(1) First, a cyclic ester compound is subjected to a polymerization reaction using a polymerization catalyst in the presence of the above hydroxymonocarboxylic acid derivative in which the carboxyl group is protected (e.g., tert-butyl D-lactate or benzyl L-lactate), or a hydroxydicarboxylic acid derivative in which the carboxyl groups are protected (e.g., dibenzyl tartronate or di-tert-butyl 2-hydroxyethylmalonate).

Examples of the above "hydroxymonocarboxylic acid derivative in which the carboxyl group is protected" or the "hydroxydicarboxylic acid derivative in which the carboxyl groups are protected" include a hydroxycarboxylic acid derivative in which the carboxyl group (—COOH) is amidated (—CONH$_2$) or esterified (—COOR), and a hydroxycarboxylic acid derivative in which the carboxyl group (—COOH) is esterified (—COOR) is preferable.

Examples of R in the ester here include C$_{1-6}$ alkyl groups such as a methyl, ethyl, n-propyl, isopropyl, n-butyl or tert-butyl group, C$_{3-8}$ cycloalkyl groups such as a cyclopentyl or cyclohexyl group, C$_{6-12}$ aryl groups such as a phenyl or a-naphthyl group, phenyl-C$_{1-2}$ alkyl groups such as a benzyl or phenethyl group, and C$_{7-14}$ aralkyl groups such as an α-naphthylmethyl group or other α-naphthyl-C$_{1-2}$ alkyl groups. A tert-butyl group and benzyl group are particularly preferable.

The "cyclic ester compound" refers to, for example, a cyclic compound having at least one ester bond in the ring. Specific examples include cyclic monoester compounds (lactones) and cyclic diester compounds (lactides).

Examples of the "cyclic monoester compounds" include 4-member ring lactones (such as β-propiolactone, β-butyrolactone, β-isovalerolactone, β-caprolactone, 5-isocaprolactone and β-methyl-β-valerolactone), 5-member ring lactones (such as γ-butyrolactone and γ-valerolactone), 6-member ring lactones (such as δ-valerolactone), 7-member ring lactones (such as ε-caprolactone), p-dioxanone and 1,5-dioxepan-2-one.

Examples of the "cyclic diester compounds" include compounds represented by the following formula:

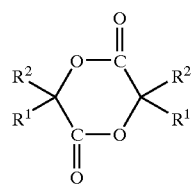

(wherein, R$^1$ and R$^2$ may be the same or different, and each represent a hydrogen atom or a C$_{1-6}$ alkyl group such as a methyl, ethyl, n-propyl, isopropyl, n-butyl or t-butyl group), and a particularly preferable example is a lactide in which R$^1$ is a hydrogen atom, R$^2$ is a methyl group or R$^1$ and R$^2$ each are a hydrogen atom.

Specific examples include glycolide, L-lactide, D-lactide, DL-lactide, meso-lactide and 3-methyl-1,4-dioxane-2,5-dione (including optically active forms).

Examples of the "polymerization catalyst" include organic tin catalysts (such as tin octylate, tin di-n-butyl dilaurate and tetraphenyl tin), aluminum catalysts (such as triethyl aluminum) and zinc catalysts (such as diethyl zinc).

From the viewpoint of ease of removal after the reaction, aluminum catalysts and zinc catalysts are preferable, and from the viewpoint of safety in the case of remaining, zinc catalysts are more preferable. Examples of solvents of polymerization catalysts employable include benzene, hexane and toluene, while hexane and toluene are preferable.

With respect to the "polymerization process", a block polymerization process, which is performed with the reactants in a melted state, or a solution polymerization process, in which the reactants are dissolved in a suitable solvent (such as benzene, toluene, xylene, decalin or dimethylformamide), should be used. Toluene and xylene are preferable examples of solvents. There are no particular restrictions on the polymerization temperature, and in the case of bulk polymerization, the polymerization temperature is that equal to or higher than the temperature in which the reactants reach the melted state at the start of the reaction, and is normally 100 to 300° C. In the case of solution polymerization, the polymerization temperature is normally from room temperature to 150° C. When the reaction temperature exceeds the boiling point of the reaction solution, either the reaction solution should be refluxed by attaching a condenser, or the reaction should be carried out in a pressure-proof container. The polymerization time is suitably determined in consideration of the polymerization temperature, other reaction conditions and physical properties of the target polymer, etc., and it is, for example 10 minutes to 72 hours. Following the reaction, the reaction mixture is dissolved in a suitable solvent (such as acetone, dichloromethane or chloroform), and after terminating the polymerization with acid (such as hydrochloric acid, acetic anhydride or trifluoroacetic acid), the reaction mixture is mixed in a solvent that does not dissolve the target product (such as alcohol, water, ether or isopropyl ether) to precipitate in accordance with conventional processss and isolate the polymer having a protected carboxyl group at its ω-end.

Instead of using a conventional so-called protic chain transfer agent such as methanol, the polymerization process of the present application uses a hydroxycarboxylic acid derivative in which the carboxyl group is protected (e.g., tert-butyl D-lactate or benzyl L-lactate) or a hydroxydicarboxylic acid derivative in which the carboxyl groups are protected (e.g., dibenzyl tartronate or tert-butyl 2-hydroxyethylmalonate).

As a result of using this type of protic chain transfer agent such as a hydroxycarboxylic acid derivative in which the carboxyl group is protected (e.g., tert-butyl D-lactate or benzyl L-lactate) or a hydroxydicarboxylic acid derivative in which the carboxyl groups are protected (e.g., dibenzyl tartronate or di-tert-butyl 2-hydroxyethylmalonate), (1) the molecular weight can be controlled according to the charged composition, and (2) the carboxyl group at the ω-end of the resulting biodegradable polymer can be liberated as a result of subjecting to a deprotecting reaction following polymerization.

(2) Next, the target biodegradable polymer having a free carboxyl group at its ω-end can be obtained by subjecting the polymer having a protected carboxyl group at its ω-end obtained by the polymerization reaction of (1) above to a deprotecting reaction.

The protecting group can be eliminated by a process which is itself known. Although any process may be used for this process provided it is a process that allows the protecting group to be removed without having an effect on the ester bond of the poly(hydroxycarboxylic acid), specific examples of such a process include reduction and acidolysis (reactions).

Examples of the reduction processss include catalytic reduction that uses a catalyst (such as palladium carbon, palladium black and platinum oxide), reduction by sodium in liquid ammonia, and reduction by dithiothreitol. For example, in the case of catalytic reduction of a polymer having a carboxyl group protected with a benzyl group at its ω-end, deprotecting can be specifically carried out by adding palladium carbon to a solution in which the polymer is dissolved in ethyl acetate, dichloromethane or chloroform, followed by aerating for about 20 minutes to about 4 hours with hydrogen at room temperature while stirring vigorously.

Examples of acidolysis processss include acidolysis by inorganic acid (such as hydrogen fluoride, hydrogen bromide and hydrogen chloride), organic acid (such as trifluoroacetic acid, methanesulfonic acid and trifluoromethanesulfonic acid) or their mixtures. In addition, a cation scavenger (such as anisole, phenol and thioanisole) may be suitably added during acidolysis as necessary. For example, in the case of acidolysis of a polymer having a carboxyl group protected with a tert-butyl group at its ω-end, deprotecting is specifically carried out by adding a suitable amount of trifluoroacetic acid to a solution of the polymer dissolved in dichloromethane, xylene or toluene, or dissolving the polymer in trifluoroacetic acid, followed by stirring for about one hour at room temperature.

Preferably, the acidolysis may be performed immediately after the polymerization reaction, and in such case, it can also be used as the reaction for terminating polymerization.

Moreover, by subjecting the polymer obtained by the above deprotecting reaction to an acid hydrolysis reaction as necessary, the weight average molecular weight, number average molecular weight or amount of terminal carboxyl group of the polymer can be adjusted according to the objective. More specifically, this can be carried out using, for example, the process described in EP-A-0839525 or a process conforming to it.

The biodegradable polymer obtained in the manner described above can be used as the base for producing a sustained-release preparation.

The weight ratio of physiologically active substance to the base of the present invention is, in the case of a peptide, for example, about 0.001 to about 50% (w/w), preferably about 0.02 to about 40% (w/w) and more preferably about 0.1 to 30% (w/w), and in the case of a non-peptide, about 0.01 to 80% (w/w), and preferably about 0.1 to 50% (w/w).

(3) A sustained-release preparation containing a biodegradable polymer obtained by the production process of the present invention is produced by, for example, aqueous drying, phase separation, spray drying or processss that comply with these processss.

The following provides a description of a production process in the case of producing a sustained-release preparation in the form of, for example, microcapsules (also referred to as microspheres).

Drug retention agents (such as gelatin, hydroxynaphthoic acid and salicylic acid) may also be added as necessary during the following production process in accordance with processss which are themselves known.

(I) Aqueous Drying Process (i) O/W Process

In this process, first an organic solvent solution of biodegradable polymer is prepared. Organic solvents used when producing the sustained-release preparation of the present invention preferably have a boiling point of 120° C. or lower.

Examples of the organic solvents employable are used include halogenated hydrocarbons (such as dichloromethane, chloroform, dichloroethane, trichloroethane and carbon tetrachloride), ethers (such as ethyl ether and isopropyl ether), fatty acid esters (such as ethyl-acetate and butyl acetate), aromatic hydrocarbons (such as benzene, toluene and xylene), alcohols (such as ethanol and methanol) and acetonitrile. Halogenated hydrocarbons are preferable, and dichloromethane is particularly preferable. In addition, these may also be mixed in suitable proportions. In this case, a mixed liquid of halogenated hydrocarbon and alcohol is preferable, and a mixed liquid of dichloromethane and ethanol is particularly preferable.

While the concentration of biodegradable polymer in the organic solvent solution varies according to the molecular weight of the biodegradable polymer and type of organic solvent, for example, in the case of using dichloromethane as the organic solvent, the concentration is typically selected from about 0.5 to about 70 wt %, more preferably about 1 to about 60 wt %, and particularly preferably about 2 to about 50 wt %.

The ratio of both solvents in the case of using ethanol as the organic solvent mixed with dichloromethane is typically selected from about 0.01 to about 50% (v/v), more preferably about 0.05 to about 40% (v/v) and particularly preferably about 0.1 to about 30% (v/v).

A physiologically active substance is then added, dissolved or dispersed in the organic solvent solution of biodegradable polymer obtained in this manner. At this time, the amount of physiologically active substance added is such that the upper limit of the weight ratio of physiologically active substance: biodegradable polymer is up to about 1:1, and preferably up to about 1:2.

Next, the resulting organic solvent solution containing a composition consisting of a physiologically active substance or its salt and biodegradable polymer is added to an aqueous phase, and after forming an oil (oil phase)/water (aqueous phase) emulsion, the solvent in the oil phase is evaporated to prepare microcapsules. The volume of the aqueous phase at this time is typically selected from about 1 to about 10,000 times the volume of the oil phase, preferably about 5 to about 5,000 times and particularly preferably about 10 to about 2,000 times.

An emulsifier may also be added to the outer aqueous phase. Any emulsifier may be used as the emulsifier provided it typically allows the formation of a stable O/W emulsion. Specific examples of emulsifiers employable include anionic surfactants (such as sodium oleate, sodium stearate and sodium laurate), nonionic surfactants (such as polyoxyethylene sorbitan fatty acid ester (e.g., Tween 80, Tween 60 available from Atlas Powder), polyoxyethylene castor oil derivatives (HCO-60 and HCO-50 available from Nikko Chemicals)), polyvinylpyrrolidone, polyvinyl alcohol, carboxymethyl cellulose, lecithin, gelatin and hyaluronic acid. One kind of these or a combination of several kinds may be used. The concentration at the time of use is preferably within the range of about 0.01 to 10 wt %, and more preferably within the range of about 0.05 to about 5 wt %.

In addition, an osmotic pressure regulator may also be added to the above-described outer aqueous phase. The osmotic pressure regulator should be that which exhibits osmotic pressure in the case of being in the form of an aqueous solution.

Examples of the osmotic pressure regulator include polyhydric alcohols, monohydric alcohols, monosaccharides, disaccharides, oligosaccharides and amino acids or their derivatives.

Examples of the above polyvalent alcohols employable include trihydric alcohols such as glycerin, pentahydric alcohols such as arabitol, xylitol and adonitol, and hexahydric alcohols such as mannitol, sorbitol and dulcitol. Among these, hexahydric alcohols are preferable, and mannitol is particularly preferable.

Examples of the above monohydric alcohols include methanol, ethanol and isopropyl alcohol, and among these, ethanol is preferable.

Examples of the above monosaccharides employable include pentoses such as arabinose, xylose, ribose and 2-deoxyribose, and hexoses such as glucose, fructose, galactose, mannose, sorbose, rhamnose and fucose, and among these, hexoses are preferable.

Examples of the above oligosaccharides employable include trisaccharides such as maltotriose and raffinose, and tetrasaccharides such as stachyose, and trisaccharides are preferable.

Examples of above monosaccharide, disaccharide and oligosaccharide derivatives employable include glucosamine, galactosamine, glucuronic acid and galacturonic acid.

Any amino acids can be used provided they are of the L-form, examples of which include glycine, leucine and arginine, with L-arginine being preferable.

These osmotic pressure regulators may be used alone or as a mixture.

These osmotic pressure regulators are used at a concentration such that the osmotic pressure of the outer aqueous phase is about 1/50 to about 5 times, and preferably about 1/25 to about 3 times, the osmotic pressure of physiological saline.

A process which is itself known or a process that complies with such is used for the process of removing an organic solvent. Examples of such processs include a process whereby an organic solvent is evaporated at normal pressure or while gradually decreasing pressure under stirring with a propeller stirrer or magnetic stirrer and a process whereby organic solvent is evaporated while adjusting vacuum using a rotary evaporator and so forth.

After separating the microcapsules obtained in this manner by centrifugal separation or filtration, a free physiologically active substance, an emulsifier and so forth adhered to the surface of the microcapsules are washed off by repeatedly washing several times with distilled water, again dispersing in distilled water and so forth and then freeze-drying.

An anticoagulant may be added during the production process to prevent particles from aggregating. Examples of the anticoagulants employable used include water-soluble polysaccharides such as mannitol, lactose, glucose and starch (e.g., cornstarch), amino acids such as glycine, and proteins such as fibrin and collagen. Of them, mannitol is particularly preferable.

In addition, moisture and an organic solvent within the microcapsules may be removed by heating under conditions at which the microcapsules do not melt and adhere to each other under reduced pressure as necessary following freeze-drying. Preferably, the microcapsules are heated at a temperature slightly higher than the midpoint glass transition temperature of the biodegradable polymer as determined with a differential scanning calorimeter under conditions of heating at the rate of 10 to 20° C. per minute. More preferably, the microcapsules are heated within a temperature range that is about 30° C. higher than the midpoint glass transition temperature of the biodegradable polymer. In the case of using a lactic acid-glycolic acid polymer for the biodegradable polymer in particular, the microcapsules are preferably heated within a temperature range from its midpoint glass transition temperature to 10° C. higher than the midpoint glass transition temperature, and more preferably are heated within a temperature range from its midpoint glass transition temperature to 5° C. higher than the midpoint glass transition temperature.

Although heating time varies according to the amount of microcapsules and so forth, in general, heating is performed for about 12 to about 168 hours, preferably for about 24 to about 120 hours, and particularly preferably for about 48 hours to about 96 hours, after the microcapsules themselves have reached a prescribed temperature.

There are no particular restrictions on the heating process provided it is a process that allows the collection of microcapsules to be heated uniformly.

Examples of the heating and drying processs employable include heating and drying in a constant temperature bath, fluid bath, moving bath or kiln, and heating and drying with microwaves. Heating and drying in a constant temperature bath is preferable.

(ii) W/O/W Process

First, an organic solvent solution of biodegradable polymer is prepared.

Examples of the organic solvents employable include halogenated hydrocarbons (such as dichloromethane, chloroform, dichloroethane, trichloroethane and carbon tetrachloride), ethers (such as ethyl ether and isopropyl ether), fatty acid esters (such as ethyl acetate and butyl acetate), aromatic hydrocarbons (such as benzene, toluene and xylene), alcohols (such as ethanol and methanol) and acetonitrile. Among them, halogenated hydrocarbons are preferable, and dichloromethane is particularly preferable. These may also be mixed in suitable proportions. In this case, a mixed liquid of halogenated hydrocarbon and alcohol is preferable, while a mixed liquid of dichloromethane and ethanol is particularly preferable.

The concentration of biodegradable polymer in the organic solvent solution varies according to the molecular weight of the biodegradable polymer and type of organic solvent, and, for example, in the case of using dichloromethane for the organic solvent, the concentration is typically selected from about 0.5 to about 70 wt %, more preferably about 1 to about 60 wt %, and particularly preferably about 2 to about 50 wt %.

Next, a solution of a physiologically active substance or its salt (examples of the solvent include water and mixtures of water and alcohol (e.g., methanol or ethanol)) is added to the organic solvent solution of biodegradable polymer (oil phase). This mixture is then emulsified by a known process such as the use of a homogenizer or ultrasonic waves) to form a W/O emulsion.

Next, the resulting W/O emulsion composed of physiologically active substance and biodegradable polymer is added to an aqueous phase to form a W (internal aqueous phase)/O (oil phase)/W (external aqueous phase) emulsion followed by evaporating the solvent in the oil phase to prepare microcapsules. The volume of the external aqueous phase at this time is typically selected from about 1 to about 10000 times, more preferably about 5 to 5,000 times, and particularly preferably about 10 to about 2,000 times, the volume of the oil phase.

Emulsifiers and osmotic pressure regulators that may be added to the above external aqueous phase along with other aspects of the preparation process are the same as described in part (i) of the above section (I).

(II) Phase Separation Process

In the case of preparing microcapsules according to this process, the microcapsules are precipitated and solidified by gradually adding while stirring a coacervation agent to the organic solvent solution containing a composition comprised of physiologically active substance and biodegradable polymer described in the aqueous drying process of the above section (I). The coacervation agent is selected to be about 0.01 to 1,000 times, preferably about 0.05 to 500 times, and particularly preferably about 0.1 to 200 times the volume of the oil phase.

There are no particular restrictions on the coacervation agent provided it is a polymer-based, mineral oil-based or vegetable oil-based compound that is mixed with an organic solvent and does not dissolve the biodegradable polymer. Specific examples of coacervation agents employable include silicone oil, sesame oil, soybean oil, corn oil, cottonseed oil, coconut oil, linseed oil, mineral oil, n-hexane and n-heptane. Two or more kinds of these may be used as a mixture.

After separating the microcapsules obtained in this manner, they are repeatedly washed with heptane and so forth to remove the coacervation agent and so forth other than that of the composition comprising physiologically active substance and biodegradable polymer followed by freeze-drying. Alternatively, the microcapsules may be freeze-dried or heat-dried after washing in the same manner as described in the aqueous drying process of part (i) of the above section (I).

(III) Spray Drying Process

In the case of producing microcapsules according to this process, an organic solvent solution or dispersion containing a composition composed of the two elements of physiologically active substance and biodegradable polymer described in the aqueous drying process of the above section (I) is sprayed into the drying chamber of a spray dryer using a nozzle to enable the organic solvent within the fine droplets to be evaporated and microcapsules to be prepared in an extremely short amount of time. Examples of the nozzle include a two fluid nozzle, pressure nozzle and rotary disk. Subsequently, the microcapsules may be freeze-dried or heat-dried after washing according to the same process as described in the aqueous drying process of the above section (I) as necessary.

Another example of a drug form in addition to the microcapsules described above are fine particles (microparticles). These fine particles are formed by preparing an organic solvent solution or dispersion containing a composition comprised of physiologically active substance and biodegradable polymer as described in the aqueous drying process of section (I) pertaining to the production of microcapsules, evaporating the organic solvent and water while adjusting the degree of vacuum using a rotary evaporator and so forth to dry to a solid, and finally crushing with a jet mill and so forth.

Moreover, the crushed fine particles may be freeze-dried or heat-dried after washing according to the same process as described in the aqueous drying process of section (I) pertaining to the production of microcapsules.

The microcapsules or fine particles obtained here are able to achieve drug release corresponding to the rate of decomposition of the biodegradable polymer or lactic acid-glycolic acid polymer used.

The sustained-release composition obtained by the production process of the present invention can be prepared in various drug forms by either using as such or using as their raw material substances, and can be administered as an injection or implant when administering intramuscularly, subcutaneously or into an organ, as a transmucosal preparation when administering into the nasal cavity, rectum or uterus, or as an oral preparation (such as capsules (e.g., hard capsules and soft capsules), solid preparations such as granules and powders, or liquid preparations such as syrups, emulsions and suspensions).

For example, in order to:produce a sustained-release composition obtained according to the production process of the present invention in the form of an injection, these are made into a sustained-release injection that can actually be used by either preparing in the form of an aqueous suspension with a dispersant (for example, a surfactant such as Tween 80 or HCO-60, or polysaccharide such as sodium hyaluronate, carboxymethyl cellulose or sodium alginate), preservative (for example, methyl paraben or propyl paraben) or isotonic agent (for example, sodium chloride, mannitol, sorbitol, glucose or proline), or in the form of an oily suspension by dispersing with a vegetable oil such as sesame oil or corn oil.

The particle size of a sustained-release composition obtained according to the production process of the present invention, in the case of using as a suspended injection, should be within a range that satisfies its degree of dispersion and properties of passing through needles, and, in terms of the mean particle size, should be about 0.1 to 300 μm, preferably within the range of about 0.5 to 150 μm, and more preferably within the range of about 1 to 100 μm. The mean particle size can be measured by a process which itself is known using, for example, a laser analysis type of particle size distribution measuring system (SALD2000A: Shimadzu).

In the case of making the sustained-release composition obtained by the production process of the present invention in the form of a sterile preparation, there are no particular restrictions on the process, examples of which include a process in which the entire production process is sterile, a process in which sterilization is performed with gamma rays, and a process in which an antiseptic is added.

Since the sustained-release composition of the present invention has low toxicity, it can also be used as a safe pharmaceutical for mammals (e.g., humans, cows, pigs, dogs, cats, mice, rats and rabbits).

The sustained-release composition obtained according to the production process of the present invention can be used as an agent for prevention and/or treatment of various diseases depending on the type of physiologically active substance contained, in the case the physiologically active substance is, for example, an LH-RH derivative, it can be used as an agent for the prevention and/or treatment of hormone-dependent diseases, and particularly sex hormone-dependent diseases such as sex hormone-dependent cancers (such as prostatic cancer, uterine cancer, breast cancer and pituitary tumors), prostatic hypertrophy, endometriosis, hysteromyoma, precocious puberty, dysmenorrhea, amenorrhea, premenstrual syndrome and multilocular ovarian syndrome, as well as contraceptives (or for the prevention and/or treatment of infertility in the case of utilizing the rebound effect following their discontinuance). Moreover, although non-sex hormone-dependent, it can also be used as an agent for the prevention and/or treatment of benign or malignant tumors that are LH-RH sensitive.

The dose of the sustained-release composition obtained according to the production process of the present invention varies according to the type and content of the principal agent in the form of the physiologically active substance, the drug form, the duration of release of physiologically active substance, target disease, target animal and so forth, it should be an effective amount of the physiologically active substance. The adult dose of principal agent in the form of the physiologically active substance per administration in the case of, for example, the duration of release of the sustained-release preparation being six months, can be suitably selected from a range of preferably about 0.01 mg to 10 mg/kg of body weight, and more preferably, about 0.05 mg to 5 mg/kg of body weight.

The adult dose of sustained-release composition per administration can be suitably selected from a range of preferably about 0.05 mg to 50 mg/kg of body weight, and more preferably, about 0.1 mg to 30 mg/kg of body weight.

The number of administrations can be suitably selected according to the type and content of principal agent in the form of the physiologically active substance, drug form, duration of release of the physiologically active substance, target disease, target animal and so forth, such as once every several weeks, once a month or once every several months (such as once every 3 months, once every 4 months or once every 6 months).

EXAMPLES

The present invention will be described more specifically by way of its examples, comparative examples and experiment examples, but the present invention is not limit to them.

Example 1
Synthesis of PLA by [tert-butyl D-lactate/diethyl zinc/DL-lactide]

A toluene solution of diethyl zinc (1/2 mol equivalent) was added to 40.6 mg of tert-butyl D-lactate cooled to −78° C. in a nitrogen atmosphere, followed by reacting for 30 minutes at room temperature. The resulting mixture was then admixed with 4.14 g of melted DL-lactide in a nitrogen atmosphere, followed by polymerizing at 130° C. for 2 hours.

The reactants were dissolved in dichloromethane to terminate the polymerization reaction. After mixing with a 0.1 N aqueous solution of HCl and stirring for 20 minutes, washing with water was repeated until the mixture became neutral. Next, the dichloromethane solution was concentrated and vacuum-dried (40° C., 2 days) to obtain poly(DL-lactic acid) in which the ω residue is tert-butyl D-lactate. As a result of $^1$H-NMR analysis, methine hydrogen of the lactic acid residue (5.1–5.3 ppm), methyl group hydrogen (1.5–1.6 ppm) and tert-butyl group hydrogen (1.46 ppm) were confirmed. When a terminal group labeling assay process was applied to this polymer, the polymer hardly demonstrated any color. On the basis of these findings, the ω residue of the polymer was indicated to be lactic acid in which the carboxyl group was protected with a tert-butyl group.

Next, in order to remove the protecting group, this polymer was dissolved in trifluoroacetic acid and stirred overnight at room temperature. Subsequently, the solution was mixed with cold isopropyl ether, the polymer was precipitated and collected, and re-precipitation purification was performed twice with dichloromethane/cold isopropyl ether. The purified precipitate was dissolved in dichloromethane and repeatedly washed with water until it became neutral. Next, the dichloromethane solution was concentrated and vacuum-dried (40° C., 2 days) to obtain 3.84 g of poly(DL-lactic acid) in which the ω residue is D-lactic acid. As a result of $^1$H-NMR analysis, the signal corresponding to the tert-butyl group had completely disappeared, thereby confirming that the protecting group had been removed. In addition, as a result of measuring atomic absorption, the amount of zinc remaining was below the detection limit (10 ppm), thereby indicating that the polymerization catalyst can be effectively removed with this process. Moreover, when a terminal group labeling assay process was applied to this polymer, the polymer demonstrated an intense violet color, thereby confirming regeneration of the carboxyl group as a result of deprotecting. As a result of GPC, the weight average molecular weight was 43.0 kDa, and the number average molecular weight was 15.9 kDa.

Example 2
Synthesis of PLA by [tert-butyl D-lactate/diethyl zinc/DL-lactide]

A toluene solution of diethyl zinc (1/2 mol equivalent) was added to tert-butyl D-lactate cooled to −78° C. in a nitrogen atmosphere, followed by reacting for 10 to 30 minutes at room temperature. The resulting mixture was then admixed with melted DL-lactide in a nitrogen atmosphere, and then polymerized at 130° C. for 1 to 5 hours.

The reactants were dissolved in trifluoroacetic acid to terminate the polymerization reaction and remove the protecting group, followed by stirring for one hour at room temperature. Subsequently, the polymer was precipitated and collected by mixing with cold isopropyl ether, after which re-precipitation purification was performed twice with dichloromethane/cold isopropyl ether. The purified precipitate was dissolved in dichloromethane and repeatedly washed with water until it became neutral. Next, the dichloromethane solution was concentrated and vacuum-dried (40° C., 2 days) to obtain poly(DL-lactic acid) in which the ω residue is D-lactic acid. As a result of $^1$H-NMR analysis, the signal corresponding to the tert-butyl group had completely disappeared, and the protecting group was confirmed to have been removed on the basis of this finding. In addition, as a result of measuring atomic absorption, the amount of zinc remaining was found to be below the detection limit (10 ppm), thereby indicating that the polymerization catalyst can be effectively removed with this process. Moreover, when a terminal group labeling assay process was applied to this polymer, the polymer demonstrated an intense violet color, thereby confirming regeneration of the carboxyl group as a result of deprotecting. Table 1 shows the charged compositions of DL-lactide and tert-butyl D-lactate, the molar ratios, as well as the weight average molecular weight of the polymer and amount of carboxyl group after deprotecting. As is clear from the table, the molecular weight of the polymer can be controlled according to the charged molar ratio of DL-lactide and tert-butyl D-lactate.

TABLE 1

| Run No. | DL-lactide (M) (g) | Tert-butyl D-lactate (I) (mg) | M/I (mol/mol) | Mw (kDa) | [COOH] (μmol/g) |
|---|---|---|---|---|---|
| PA1 | 7.89 | 167.1 | 47.9 | 19.8 | 97.0 |
| PA2 | 22.38 | 219.4 | 103.5 | 34.8 | 54.5 |
| PA3 | 8.09 | 79.3 | 103.5 | 35.8 | 49.6 |
| PA4 | 10.16 | 94.0 | 109.7 | 37.9 | 52.7 |
| PA5 | 10.83 | 93.6 | 117.3 | 40.1 | 47.4 |
| PA6 | 11.11 | 90.7 | 124.3 | 40.0 | 47.0 |
| PA7 | 10.92 | 84.4 | 131.2 | 43.3 | 46.0 |
| PA8 | 11.49 | 84.3 | 138.2 | 43.5 | 44.4 |
| PA9 | 12.10 | 84.6 | 145.1 | 44.4 | 42.3 |

Example 3
Synthesis of PLA by [Benzyl L-lactate/diethyl zinc/DL-lactide]

A toluene solution of diethyl zinc (1/2 mol equivalent) was added to 181.7 mg of benzyl L-lactate cooled to −78° C. in a nitrogen atmosphere, followed by reacting at room temperature for 20 minutes. After diluting by addition of 1 ml of distilled toluene, 15.03 g of DL-lactide was added in a nitrogen atmosphere and polymerized at 130° C. for 1.5 hours.

The reactants were dissolved in dichloromethane to terminate the polymerization reaction. After mixing with a 0.1 N aqueous solution of HCl and stirring for 20 minutes, washing with water was repeated until the mixture became neutral. Next, the dichloromethane solution was concentrated and vacuum-dried (40° C., 2 days) to obtain poly(DL-lactic acid) in which the ω residue is benzyl L-lactate. As a result of ¹H-NMR analysis, methine hydrogen of the lactic acid residue (5.1–5.3 ppm), methyl group hydrogen (1.5–1.6 ppm) and phenyl hydrogen of the benzyl group (7.35 ppm) were confirmed. In addition, when a terminal group labeling assay process was applied to this polymer, the polymer hardly demonstrated any color. On the basis of these findings, the ω residue of the polymer was indicated to be lactic acid in which the carboxyl group was protected with a benzyl group.

Next, in order to remove the protecting group, about half of this polymer was dissolved in 30 ml of trifluoroacetic acid followed by the addition of thioanisole (at 3 equivalents of benzyl L-lactate) and stirred for one hour while cooling with ice. This was followed by the addition of methanesulfonic acid and stirring for further 2 hours while cooling with ice. The reaction liquid was then mixed with cold isopropyl ether, and after precipitating and collecting the polymer, re-precipitation purification was performed twice with dichloromethane/cold isopropyl ether. The purified precipitate was dissolved in dichloromethane and repeatedly washed with water until it became neutral. Next, the dichloromethane solution was concentrated and vacuum-dried (40° C., 2 days) to obtain 7.54 g of poly(DL-lactic acid) in which the ω residue is L-lactic acid. As a result of ¹H-NMR analysis, the signal corresponding to the phenyl hydrogen of the benzyl group had completely disappeared, thereby confirming that the protecting group had been removed. In addition, as a result of measuring atomic absorption, the amount of zinc remaining was below the detection limit (10 ppm), thereby indicating that the polymerization catalyst can be effectively removed with this process. Moreover, when a terminal group labeling assay process was applied to this polymer, the polymer demonstrated an intense violet color, thereby confirming regeneration of the carboxyl group as a result of deprotecting.

Example 4
Synthesis of PLA by [Benzyl L-lactate/diethyl zinc/DL-lactide]

A solution (hexane or toluene) of diethyl zinc (1/2 mol equivalent) was added to benzyl L-lactate cooled to −78° C. in a nitrogen atmosphere, followed by reacting at room temperature for 20 minutes. The resulting mixture was then admixed with melted DL-lactide in a nitrogen atmosphere, and then polymerized at 130° C. for 1.5 hours.

Next, the reactants were dissolved with 30 ml of trifluoroacetic acid to terminate the polymerization reaction and remove the protecting group, followed by the addition of thioanisole (at 3 equivalents of benzyl L-lactate) and stirring for one hour while cooling with ice. Although QA2 was used directly in the next step, QA1 was additionally stirred for one hour at room temperature. The reaction liquid was then mixed with cold isopropyl ether and the polymer was precipitated and collected, after which re-precipitation purification was performed twice with dichloromethane/cold isopropyl ether. The purified precipitate was dissolved in dichloromethane and repeatedly washed with water until it became neutral. Next, the dichloromethane solution was concentrated and vacuum-dried (40° C., 2 days) to obtain poly(DL-lactic acid) in which the ω residue is L-lactic acid. As a result of ¹H-NMR analysis, the signal corresponding to the phenyl hydrogen of the benzyl group had completely disappeared, and the protecting group was confirmed to have been removed on the basis of this finding. In addition, as a result of measuring atomic absorption, the amount of zinc remaining was found to be below the detection limit (10 ppm), thereby indicating that the polymerization catalyst can be effectively removed with this process. Moreover, when a terminal group labeling assay process was applied to this polymer, the polymer demonstrated an intense violet color, thereby confirming regeneration of the carboxyl group as a result of deprotecting. The results of synthesis are shown in Table 2.

TABLE 2

| Run No. | DL-lactide (M) (g) | Benzyl L-lactate (I) (mg) | M/I (mol/mol) | Mw (kDa) | [COOH] (μmol/g) |
|---|---|---|---|---|---|
| QA1 | 12.13 | 146.6 | 82.8 | 36.0 | 70.4 |
| QA2 | 10.55 | 127.4 | 103.5 | 44.6 | 46.1 |

Example 5
Synthesis of Tartronic Acid Terminal PLA by [Dibenzyl tartronate/diethyl zinc/DL-lactide]

A hexane solution of diethyl zinc (1/2 mol equivalent) was added to 592.8 mg of dibenzyl tartronate cooled to −78° C. in a nitrogen atmosphere, followed by reacting for 20 minutes at room temperature. 9.63 g of DL-lactide were admixed with this mixture in a nitrogen atmosphere followed by polymerizing at 130° C. for 3 hours.

The reactants were dissolved in dichloromethane to terminate the polymerization reaction. After mixing with a 0.1 N aqueous HCl solution and stirring for 20 minutes, washing with water was repeated until the mixture became neutral. Next, the dichloromethane solution was concentrated and vacuum-dried (40° C., 2 days) to obtain poly(DL-lactic acid) in which the ω residue is dibenzyl tartronate. As a result of ¹H-NMR analysis, methine hydrogen of the lactic acid residue (5.1–5.3 ppm), methyl group hydrogen (1.5–1.6 ppm) and phenyl hydrogen of the benzyl group (7.35 ppm) were confirmed. In addition, when a terminal group labeling assay process was applied to this polymer, the polymer hardly demonstrated any color. On the basis of these findings, the ω residue of the polymer was indicated to be tartronic acid in which the carboxyl group was protected with a benzyl group.

Next, in order to remove the protecting group, 215 mg of this polymer were dissolved with 2 ml of trifluoroacetic acid followed by the addition of 200 μl of thioanisole and stirring at −5° C. for one hour. This was followed by the addition of 2 ml of methanesulfonic acid, stirring for 20 minutes while cooling with ice and additionally stirring for 25 minutes at room temperature. The reaction liquid was then mixed with cold isopropyl ether, and after precipitating and collecting the polymer, re-precipitation purification was performed twice with dichloromethane/cold isopropyl ether. The purified precipitate was dissolved in dichloromethane and repeatedly washed with water until it became neutral. Next, the dichloromethane solution was concentrated and vacuum-dried (40° C., 2 days) to obtain poly(DL-lactic acid) in which the ω residue is tartronic acid. As a result of ¹H-NMR analysis, the signal corresponding to the phenyl hydrogen of the benzyl group had completely disappeared, thereby confirming that the protecting group had been removed. In addition, as a result of measuring atomic absorption, the amount of zinc remaining was below the detection limit (10 ppm), thereby indicating that the polymerization catalyst can be effectively removed with this process. Moreover, when a terminal group labeling assay process was applied to this polymer, the polymer demonstrated an intense violet color, thereby confirming regeneration of the carboxyl group as a result of deprotecting.

Example 6
Synthesis of Tartronic Acid Terminal PLA by [Dibenzyl tartronte/diethyl zinc/DL-lactide]

A toluene solution of diethyl zinc (1/2 mol equivalent) was added to dibenzyl tartronate cooled to −78° C. in a nitrogen atmosphere, followed by reacting for 20 minutes at room temperature. DL-lactide was then admixed with this mixture in a nitrogen atmosphere, and then polymerized at 130° C. for 1 to 5 hours.

Next, the reactants were dissolved in 30 ml of trifluoroacetic acid to terminate the polymerization reaction and remove the protecting group, followed by the addition of thioanisole (at 3 equivalents of benzyl L-lactic acid) and stirring at −5° C. for one hour. Methanesulfonic acid was then added and the mixture was additionally stirred for 2 hours while cooling with ice. The reaction liquid was mixed with cold isopropyl ether, and the polymer was precipitated and collected after which re-precipitation purification was performed twice with dichloromethane/cold isopropyl ether. The purified precipitate was dissolved in dichloromethane and repeatedly washed with water until it became neutral. Next, the dichloromethane solution was concentrated and vacuum-dried (40° C., 2 days) to obtain poly(DL-lactic acid) in which the ω residue is tartronic acid. As a result of $^1$H-NMR analysis, the signal corresponding to the phenyl hydrogen of the benzyl group had completely disappeared, and the protecting group was confirmed to have been removed on the basis of this finding. In addition, as a result of measuring atomic absorption, the amount of zinc remaining was found to be below the detection limit (10 ppm), thereby indicating that the polymerization catalyst can be effectively removed with this process. Moreover, when a terminal group labeling assay process was applied to this polymer, the polymer demonstrated an intense violet color, thereby confirming regeneration of the carboxyl group as a result of deprotecting. In addition, based on a comparison with the absorbance when tartronate hydrazide was obtained by the ONPH labeling process using tartronic acid as the standard substance, the amount of tartronic acid, which is the ω residue of the polymer, was determined as the amount of the dicarboxyl group. The results of the synthesis are shown in Table 3.

TABLE 3

| Run No. | DL-lactide/dibenzyl tartronate (mol/mol) | Mw (kDa) | Dicarboxyl ($\mu$mol/g) |
|---|---|---|---|
| RA1 | 6.1 | 3.6 | 378.9 |
| RA2 | 9.6 | 5.6 | 277.9 |
| RA3 | 20.0 | 9.6 | 155.3 |
| RA4 | 33.9 | 20.2 | 94.3 |
| RA5 | 68.5 | 25.9 | 66.2 |
| RA6 | 103.2 | 34.2 | 44.5 |

Example 7
Synthesis of 2-hydroxyethylmalonic Acid Terminal PLA by [di-tert-butyl 2-hydroxyethylmalonate/diethyl zinc/DL-lactide]

A toluene solution of diethyl zinc (1/2 mol equivalent) was added to 482.4 mg of di-tert-butyl 2-hydroxyethylmalonate cooled to −78° C. in a nitrogen atmosphere, followed by reacting at room temperature for 30 minutes. The resulting mixture was admixed with a solution of 3.43 g of melted DL-lactide in a nitrogen atmosphere followed by polymerizing at 130° C. for 2 hours.

The reactants were dissolved in dichloromethane to terminate the polymerization reaction. After mixing with a 0.1 N aqueous HCl solution and stirring for 20 minutes, washing with water was repeated until the mixture became neutral. Next, the dichloromethane solution was concentrated and vacuum-dried (40° C., 2 days) to obtain poly(DL-lactic acid) in which the ω residue is di-tert-butyl 2-hydroxyethylmalonate. As a result of $^1$H-NMR analysis, methine hydrogen of the lactic acid residue (5.1–5.3 ppm), methyl group hydrogen (1.5–1.6 ppm) and tert-butyl group hydrogen (1.46 ppm) were confirmed. In addition, when a terminal group labeling assay process was applied to this polymer, the polymer hardly demonstrated any color. On the basis of these findings, the ω-residue of the polymer was indicated to be 2-hydroxyethylmalonic acid in which the carboxyl group was protected with a tert-butyl group.

Next, the deprotecting reaction was carried out in the same manner as Example 1 to obtain 2.98 g of poly(DL-lactic acid) in which the ω residue is 2-hydroxyethylmalonic acid. As a result of $^1$H-NMR analysis, the signal corresponding to the tert-butyl group had completely disappeared, thereby confirming that the protecting group had been removed. In addition, as a result of measuring atomic absorption, the amount of zinc remaining was below the detection limit (10 ppm), thereby indicating that the polymerization catalyst can be effectively removed with this process. Moreover, when a terminal group labeling assay process was applied to this polymer, the polymer demonstrated an intense violet color, thereby confirming regeneration of the carboxyl group as a result of deprotecting.

Example 8
Synthesis of 2-hydroxyethylmalonic Acid Terminal PLA by [di-tert-butyl 2-hydroxyethylmalonate/diethyl zinc/DL-lactide]

Synthesis was performed in the same manner as Example 2 using di-tert-butyl 2-hydroxyethylmalonate instead of tert-butyl D-lactate to obtain poly(DL-lactic acid) in which the ω-end was 2-hydroxyethylmalonic acid.

As a result of $^1$H-NMR analysis, the signal corresponding to the tert-butyl group had completely disappeared, and the protecting group was confirmed to have been removed on the basis of this finding. In addition, as a result of measuring atomic absorption, the amount of zinc remaining was found to be below the detection limit (10 ppm), thereby indicating that the polymerization catalyst can be effectively removed by this process. Moreover, when a terminal group labeling assay process was applied to this polymer, the polymer demonstrated an intense violet color, thereby confirming regeneration of the carboxyl group as a result of deprotecting. In addition, based on a comparison with the absorbance when tartronate hydrazide was obtained by the ONPH labeling process using tartronic acid as the standard substance, the amount of 2-hydroxyethylmalonic acid, which is the ω residue of the polymer, was determined as the amount of the dicarboxyl group. The results of the synthesis are shown in Table 4.

TABLE 4

| Run No. | DL-lactide/di-tert-butyl 2-hydroxyethylmalonate (mol/mol) | Mw (kDa) | Dicarboxyl group ($\mu$mol/g) |
|---|---|---|---|
| SA1 | 54.5 | 16.9 | 108.1 |

Example 9
Acid Hydrolysis 800 mg of an equal mixture of polymers PA5 and PA6 synthesized in Example 2 was dissolved in 2 ml of dichloromethane, and the resulting solution was mixed with 15 ml of 1% aqueous lactic acid, followed by stirring at 65° C. The polymer was sampled at predetermined times, and after washing with water and drying, GPC measurement and terminal group labeling assay were performed. Those results are shown in Table 5. As is clear from Table 5, the amount of carboxyl group increased nearly proportional to reaction time, and the characteristics of the polymer were able to be controlled by the acid hydrolysis reaction.

TABLE 5

| Reaction time (hr) | Mw (kDa) | [COOH] ($\mu$mol/g) |
| --- | --- | --- |
| 0 | 40.6 | 46.3 |
| 2.5 | 38.0 | 50.7 |
| 5 | 35.5 | 56.1 |
| 7.5 | 32.9 | 61.0 |
| 10 | 30.1 | 67.6 |
| 24 | 18.7 | 118.5 |
| 30 | 15.2 | 145.4 |

Example 10

0.6 ml of an aqueous solution containing 0.6 g of the acetate of 5-oxo-Pro-His-Trp-Ser-Tyr-Dleu-Leu-Arg-Pro-NH—$C_2H_5$ (hereinafter abbreviated as Peptide A), and 7 ml of a dichloromethane solution containing 2.4 g of (DL-lactic acid), in which the ω residue is tartronic acid, synthesized in Example 6 (Run No. RA4) were mixed and emulsified with a homogenizer to form a W/O emulsion. Next, this emulsion was poured into 800 ml of a 0.1% (w/w) aqueous solution of polyvinyl alcohol (EG-40, The Nippon Synthetic Chemical Industry) pre-cooled to 18° C. and the mixture was stirred at 7,000 rpm using a turbine homomixer to obtain a W/O/W emulsion. After stirring this W/O/W emulsion for 3 hours at room temperature to volatize the dichloromethane and solidify the oil phase, it was filtered using a sieve having a mesh size of 75 μm after which microcapsules were separated and captured using a centrifugal separator (05PR-22, Hitachi Ltd.) under conditions of 2,000 rpm for 5 minutes. After re-dispersing the microcapsules in distilled water, the dispersion was again subjected to centrifugal separation followed by washing off free chemical and so forth. After again re-dispersing the captured microcapsules by adding a small amount of distilled water, they were freeze-dried to obtain a powder. The mass recovery rate of the microcapsules was 38%, and the Peptide A content of the microcapsules was 18.9%. The encapsulation efficiency as determined by dividing the actual content by the charged content was 94.6%.

Example 11

Microcapsules were obtained in the same manner as Example 10 with the exception of changing the composition of the W/O emulsion in Example 10 to 0.8 ml of an aqueous solution containing 0.8 g of the acetate of Peptide A, and 13 ml of a dichloromethane solution containing 3.2 g of (DL-lactic acid), in which the ω residue is tartronic acid, synthesized in Example 6 (Run No. RA6). The mass recovery rate of the microcapsules was 69%, and the Peptide A content of the microcapsules was 19.1%. The encapsulation efficiency as determined by dividing the actual content by the charged content was 95.3%.

Example 12

Microcapsules were obtained in the same manner as Example 10 with the exception of changing the composition of the W/O emulsion in Example 10 to 0.6 ml of an aqueous solution containing 0.6 g of the acetate of Peptide A, and 4 ml of a dichloromethane solution containing 2.4 g of (DL-lactic acid), in which the ω residue is 2-hydroxyethylmalonic acid, synthesized in Example B (Run No. SA1). The Peptide A content of the microcapsules was 16.3%. The encapsulation efficiency as determined by dividing the actual content by the charged content was 81.3%.

Comparative Example 1

Microcapsules were obtained in the same manner as Example 10 with the exception of changing the composition of the W/O emulsion in Example 10 to 1 ml of an aqueous solution containing 1 g of the acetate of Peptide A, and 5 ml of a dichloromethane solution containing 4 g of poly(DL-lactic acid) (PLA25000, Mw: 25.9 k, [COOH]=98.2 μmol/g, Wako Pure Chemical Industries). The mass recovery rate of the microcapsules was 49%, and the Peptide A content of the microcapsules was 11.4%. The encapsulation efficiency as determined by dividing the actual content by the charged content was 57.1%.

Experiment Example 1

Approximately 50 mg of the microcapsules obtained in Example 10 and Example 12 were dispersed in 0.3 ml of dispersant (0.15 mg of carboxymethyl cellulose, 0.3 mg of Polysorbate 80 and 15 mg of mannitol dissolved in distilled water), and the resulting dispersion was administered subcutaneously into the backs of 8-week-old male SD rats using a 22G syringe needle. The rats were sacrificed one day after administration, microcapsules remaining at the administration site were removed and the amount of Peptide A in those microcapsules was assayed. As a result, the Peptide A contents of the microcapsules were 95.6% and 87.1%, respectively.

Since the Peptide A contents obtained from Examples 10 and 12 are significantly larger than that in the case of Comparative Example 1, it is clear that the polyester of the present invention is superior as the base of a sustained-release preparation containing a high content of physiologically active substance, and according to the results of Experiment Example 1, a preparation using the polyester has the effect of inhibiting the initial release of drug following administration extremely well.

Example 13

Microcapsules were obtained in the same manner as Example 10 with the exception of changing the composition of the W/O emulsion in Example 10 to 0.8 ml of an aqueous solution containing 0.8 g of the acetate of Peptide A, and a solution to be used as the oil phase comprising 3.08 g of the polymer synthesized in Example 4 (Run No. QA1), 0.12 g of 3-hydroxy-2-naphthoic acid, 5 ml of dichloromethane and 0.3 ml of ethanol. The mass recovery rate of the microcapsules was 46%, and the Peptide A content of the microcapsules was 21.3%. The encapsulation efficiency as determined by dividing the actual content by the charged content was 106.6%.

Comparative Example 2

Microcapsules were obtained in the same manner as Example 10 with the exception of changing the composition of the W/O emulsion in Example 10 to 1 ml of an aqueous solution containing 1 g of the acetate of Peptide A, and a solution to be used as the oil phase comprising 3.85 g of poly(DL-lactic acid) (PLA25000, Mw: 25.9 k, [COOH]= 98.2 μmol/g, Wako Pure Chemical Industries), 0.15 g of 3-hydroxy-2-naphthoic acid, 5.5 ml of dichloromethane and 0.35 ml of ethanol. The mass recovery rate of the microcapsules was 49%, and the Peptide A content of the microcapsules was 21.3%. The encapsulation efficiency as determined by dividing the actual content by the charged content was 106.5%.

Comparative Example 3

Microcapsules were obtained in the same manner as Example 10 with the exception of changing the composition of the W/O emulsion in Example 10 to 0.8 ml of an aqueous solution containing 0.8 g of the acetate of Peptide A, and a solution to be used as the oil phase comprising 3.08 g of poly(DL-lactic acid) synthesized by ring-opening polymerization (Mw: 24.9 k, [COOH]=12.3 μmol/g, Boehringer-Ingelheim), 0.12 g of 3-hydroxy-2-naphthoic acid, 5.5 ml of dichloromethane and 0.3 ml of ethanol. The mass recovery rate of the microcapsules was 29%, and the Peptide A content of the microcapsules was 10.9%. The encapsulation efficiency as determined by dividing the actual content by the charged content was 54.6%.

Experiment Example 2

Approximately 40 mg of each of the microcapsules obtained in Example 13 and Comparative Example 2 were dispersed in 0.3 ml of dispersant (0.15 mg of carboxymethyl cellulose, 0.3 mg of Polysorbate 80 and 15 mg of mannitol dissolved in distilled water), and the resulting dispersion was administered subcutaneously into the backs of 8–10-week-old male SD rats with a 22G syringe needle. The rats were sacrificed at various times following administration, microcapsules remaining at the administration site were removed and the amount of Peptide A in those microcapsules was assayed. Those results are shown in Table 6.

TABLE 6

|  | Day 1 | Week 2 | Week 4 | Week 8 | Week 12 | Week 16 | Week 24 |
| --- | --- | --- | --- | --- | --- | --- | --- |
| Example 13 | 92.9% | 82.2% | 69.6% | 62.1% | 47.9% | 32.2% | 11.6% |
| Comp. Ex. 2 | 89.4% | 34.3% | 29.7% | 20.8% | — | — | — |

According to the experiment results for Example 13 and Comparative Example 2, the polyester of the present invention is an excellent base of a sustained-release preparation that contains a high content of physiologically active substance. In addition, according to the results of Experiment Example 2, a preparation that uses the polyester clearly achieves a stable release of contained drug over an extremely long period of time.

Example 14
Synthesis of PLA by [tert-butyl DL-lactate/diethyl zinc/DL-lactide]

1.242 g of tert-butyl DL-lactate was charged into a three-necked flask reaction vessel equipped with a condensation trap and having a capacity of 500 ml, and 3.8 ml of a 1.0 mol/L hexane solution of diethyl zinc was added at room temperature in a nitrogen atmosphere followed by dilution by adding 34.2 ml of dehydrated n-hexane. This was followed by the addition of 100 g of DL-lactide and stirring to obtain a uniform mixture. Heating was started and the hexane that distilled off at 65 to 70° C. was trapped outside with the condenser. The reaction was carried out for one hour at 150° C. after there was essentially no more distillation of hexane.

After dissolving the reactants in 50 ml of dichloromethane, 100 ml of trifluoroacetic acid was added to the solution to terminate the reaction and remove the protecting group followed by stirring for one hour at room temperature. Subsequently, after mixing with cold isopropyl ether and precipitating and collecting the polymer, re-precipitation purification was performed twice with dichloromethane/cold isopropyl ether. The purified precipitate was dissolved in dichloromethane and repeatedly washed with water until it became neutral. Next, the dichloromethane solution was concentrated and vacuum-dried (40° C., 2 days) to obtain poly(DL-lactic acid) in which the ω residue is DL-lactic acid. As a result of GPC measurement, Mw was 35.0 kDa and Mn was 13.6 kDa. When a terminal group labeling assay process was applied to this polymer, the polymer demonstrated an intense violet color, and a result of quantitative analysis, the amount of terminal carboxyl group was 67.7 μmol/g.

Industrial Applicability

The present invention can provide a production process of a biodegradable polymer that enables a physiologically active substance to be incorporated in a sustained-release preparation with high efficiency, has a high purity and has an extremely low level of residual catalyst. The present invention can also provide a production process of a biodegradable polymer that facilitates adjustment of the molecular weight of the target biodegradable polymer as well as the amount of free carboxyl group.

What is claimed is:

1. A process for producing a biodegradable polymer having a free carboxyl group at the ω-end comprising:
    subjecting a cyclic ester compound to a polymerization reaction in the presence of a hydroxymonocarboxylic acid derivative in which the carboxyl group is protected, or a hydroxydicarboxylic acid derivative in which the carboxyl groups are protected, and subjecting the resulting polymer having a protected carboxyl group at the ω-end to a deprotecting reaction.

2. The process according to claim 1, wherein the hydroxymonocarboxylic acid derivative in which the carboxyl group is protected is glycolic acid in which the carboxyl group is protected, L-lactic acid in which the carboxyl group is protected, D-lactic acid in which the carboxyl group is protected, or DL-lactic acid in which the carboxyl group is protected.

3. The process according to claim 1, wherein the protecting group of the hydroxymonocarboxylic acid in which the carboxyl group is protected is a tert-butyl group or benzyl group.

4. The process according to claim 1, wherein the hydroxydicarboxylic acid derivative in which the carboxyl groups are protected is dibenzyl tartronate or di-tert-butyl 2-hydroxyethylmalonate.

5. The process according to claim 1, wherein the cyclic ester compound is a cyclic monoester compound or cyclic diester compound.

6. The process according to claim 1, wherein the deprotecting reaction is an acidolysis reaction.

7. A process for producing a biodegradable polymer having a free carboxyl group at the ω-end comprising:

subjecting a cyclic ester compound to a polymerization reaction in the presence of a hydroxymonocarboxylic acid derivative in which the carboxyl group is protected, and subjecting the resulting polymer having a protected carboxyl group at the ω-end to a deprotecting reaction.

8. The process according to claim 7, wherein an acid hydrolysis reaction is carried out following the deprotecting reaction.

9. The process according to claim 1, wherein the biodegradable polymer is a biodegradable polymer that is used in a sustained-release preparation that releases a physiologically active substance over the course of at least about six months.

10. The process according to claim 7, wherein the biodegradable polymer is a biodegradable polymer that is used in a sustained-release preparation that releases a physiologically active substance over the course of at least about six months.

* * * * *